United States Patent
Spencer et al.

(10) Patent No.: US 9,078,431 B2
(45) Date of Patent: *Jul. 14, 2015

(54) METHOD FOR PREPARATION OF AN AQUEOUS GLYPHOSATE CONCENTRATE

(75) Inventors: Allan Spencer, Ferntree Gully (AU); Aristos Panayi, Taylors Hill (AU); Chad Richard Ord Sayer, Brighton (AU)

(73) Assignee: Nufarm Australia Limited, Laverton North, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/876,935

(22) PCT Filed: Sep. 30, 2011

(86) PCT No.: PCT/AU2011/001252
§ 371 (c)(1),
(2), (4) Date: Jun. 27, 2013

(87) PCT Pub. No.: WO2012/040786
PCT Pub. Date: Apr. 5, 2012

(65) Prior Publication Data
US 2013/0274103 A1    Oct. 17, 2013

Related U.S. Application Data

(60) Provisional application No. 61/388,670, filed on Oct. 1, 2010, provisional application No. 61/431,497, filed on Jan. 11, 2011.

(51) Int. Cl.
*A01N 57/20* (2006.01)
*A01N 39/04* (2006.01)
*A01N 25/02* (2006.01)
*A01N 37/10* (2006.01)

(52) U.S. Cl.
CPC .............. *A01N 25/02* (2013.01); *A01N 37/10* (2013.01); *A01N 39/04* (2013.01); *A01N 57/20* (2013.01)

(58) Field of Classification Search
CPC ....... A01N 25/02; A01N 57/20; A01N 37/10; A01N 39/04
USPC .................................................. 504/127, 206
See application file for complete search history.

(56) References Cited

U.S. PATENT DOCUMENTS

| 6,455,473 | B2 | 9/2002 | Wright |
| 6,881,707 | B2 | 4/2005 | Howat et al. |
| 2006/0040826 | A1 | 2/2006 | Eaton et al. |
| 2006/0270556 | A1 | 11/2006 | Wright et al. |
| 2009/0062123 | A1 | 3/2009 | Quick et al. |
| 2012/0231956 | A1* | 9/2012 | Rainbird ...................... 504/206 |

FOREIGN PATENT DOCUMENTS

| AU | 2007216730 B1 | 1/2009 |
| WO | 03013241 A1 | 2/2003 |
| WO | 2006023431 A2 | 3/2006 |
| WO | 2007143788 A1 | 12/2007 |
| WO | 2009075591 A1 | 6/2009 |
| WO | 2009154772 A2 | 12/2009 |

OTHER PUBLICATIONS

Search Report for GB1107525.6 (dated Sep. 28, 2011).
Search Report for GB1107540.5 (dated Sep. 28, 2011).
International Search Report for corresponding International Application No. PCT/AU2011/001252 (mailed Nov. 3, 2011).

* cited by examiner

*Primary Examiner* — John Pak
*Assistant Examiner* — Andriae M Holt
(74) *Attorney, Agent, or Firm* — LeClairRyan, a Professional Corporation

(57) ABSTRACT

A method for preparing an aqueous mixture of glyphosate salts to improve the handling of the mixture, the method comprising forming a homogeneous mixture of at least two bases comprising at least one alkali metal hydroxide, and at least one further base selected from alkali metal hydroxides and nitrogen bases and reacting the mixture of the at least two bases with glyphosate acid in an aqueous reaction medium to provide an aqueous mixture of glyphosate salts wherein the concentration of glyphosate (based on glyphosate acid equivalent) is at least 200 gae/L.

18 Claims, No Drawings

METHOD FOR PREPARATION OF AN AQUEOUS GLYPHOSATE CONCENTRATE

This application is a national stage application under 35 U.S.C. §371 of PCT Application No. PCT/AU2011/001252, filed Sep. 30, 2011, which claims the priority benefit of U.S. Provisional Patent Application Ser. Nos. 61/388,670, filed Oct. 1, 2010, and 61/431,497, filed Jan. 11, 2011.

FIELD

The invention relates to a method of preparing an aqueous concentrate of glyphosate involving neutralizing glyphosate acid with a mixture of bases including an alkali metal base. The invention further relates to a method of transport and handling of glyphosate aqueous concentrates and the use of the aqueous concentrates in controlling plant growth.

BACKGROUND

Glyphosate is commonly used and distributed as an aqueous solution of a glyphosate salt such as the isopropyl ammonium potassium or ammonium salts.

In order to reduce the transport and handling costs associated with glyphosate concentrates it is desirable to use a high loading of glyphosate, that is, the amount of active (usually expressed as glyphosate acid equivalent per liter of aqueous formulation) is desirably high within the bounds of the solubility and ability to conveniently pour and dilute the concentrate.

U.S. Pat. No. 6,544,930 (Wright) reports that high loadings can be achieved using the potassium salt of glyphosate and compositions of the potassium salt are available at loadings of 540 g acid equivalent (ae) per liter of aqueous formulation.

International Patent Publication No. WO 01/26469 discloses that aqueous formulations of glyphosate, including highly concentrated formulations, can be prepared using a mixture of glyphosate isopropyl amine and ammonium salts particularly in a weight ratio (expressed on a glyphosate ae basis) of 80:20 to 97:3.

U.S. Pat. No. 6,881,707 (Howat and Hay) reports a glyphosate composition comprising a mixture of salts of glyphosate comprising each of potassium and isopropylammonium salts. International Publication WO2006/023431 asserts that loadings of at least about 400 g glyphosate acid equivalent can be obtained by formulating in aqueous solution a mixture of salts of glyphosate at a total glyphosate ae concentration not less than about 360 gae/L, wherein (a) said glyphosate is in anionic form accompanied by low molecular weight non-amphiphilic cations in a total molar amount of about 100% to about 120% of the molar amount of said glyphosate; (b) said cations comprise potassium and propylammonium (e.g., IPA) cations in a mole ratio of about 70:30 to about 90:10; and (c) said potassium and propylammonium cations together constitute about 90 to 100 molar percent of all of said low molecular weight non-amphiphilic cations in the composition. The patent reports formulations of up to 590 g glyphosate acid equivalent per liter of aqueous formulation.

The concentrate formulation of glyphosate can be difficult to handle due to viscosity, particularly at low temperatures and high loadings of active. At high loadings the viscosity of the composition is increased to such an extent that it is often difficult to dispense the aqueous solution by pouring or pumping with normal pump equipment. Also the solution stability of the salts may be compromised, particularly at low temperatures so that precipitates form at low temperature which can not be readily resuspended or solubilised.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

We provide a method for preparing a glyphosate herbicidal aqueous concentrate to improve the handling and stability thereof, the method comprising forming a homogeneous mixture of at least two bases comprising one base selected from alkali metal hydroxides and at least one further base selected from alkali metal hydroxides and nitrogen bases and reacting the mixture of the at least two bases with glyphosate acid in an aqueous reaction medium to provide an aqueous mixture of glyphosate salts wherein the concentration of glyphosate (based on glyphosate acid equivalent which is abbreviated as "ae") is at least 200 gae/L and preferably, at least 360 gae/L.

The method uses a premix of at least one alkali metal base selected from alkali metal hydroxides and at least one further base selected from alkali metal hydroxide and nitrogen base.

The mixture of bases preferably includes at least one nitrogen base which is preferably selected from the group consisting of ammonia, ammonium hydroxide, $C_1$ to $C_{10}$ alkylamine, di-($C_1$ to $C_6$ alkyl)amine, tri-($C_1$ to $C_6$ alkyl)amine and $C_1$ to $C_{10}$ alkanolamine.

The concentration of glyphosate salts preferably is at least 450 gae/L, more preferably at least 500 gae/L, still more preferably at least 550 gae/L and still more preferably 600 gae/L, such as at least 610 gae/L, at least 620 gae/L, at least 630 gae/L and at least 640 gae/L, at least 650 gae/L, at least 660 gae/L. In one preferred set of embodiments the loading of glyphosate is in the range of from 600 to 750 gae/L particularly 600 to 700 gae/L (or up to the limit of solubility).

The alkali metal hydroxide bases are in one set of embodiments selected from at least one of sodium hydroxide, potassium hydroxide and lithium hydroxide.

In a preferred set of embodiments the mixture of bases includes at least one nitrogen base selected from the group consisting of ammonia, mono-($C_1$ to $C_8$) alkyl amines, di-($C_1$ to $C_6$) alkyl amines and tri-($C_1$ to $C_6$ alkyl) amines and more preferably from the group consisting of potassium hydroxide, ammonia, mono-($C_1$ to $C_6$) alkyl amines, di-($C_1$ to $C_6$) alkyl amines and tri-($C_1$ to $C_6$ alkyl) amines.

In one set of embodiments when the mixture of bases includes potassium hydroxide and one of ammonia or isopropylamine then at least one further base selected from said alkali metal hydroxide and said nitrogen base is present.

In a further set of embodiments the mixture of bases includes a first alkali metal hydroxide selected from sodium hydroxide, potassium hydroxide and lithium hydroxide and a second alkali metal hydroxide selected from sodium hydroxide, potassium hydroxide and lithium hydroxide.

Throughout the description and the claims of this specification the word "comprise" and variations of the word, such as "comprising" and "comprises" is not intended to exclude other additives, components, integers or steps.

In the specification and claims the terms "ae", "gae" and "kgae" in relation to glyphosate and its salts refer to acid equivalent, grams of acid equivalent and kilograms of acid equivalent respectively. The term gae/L means grams of acid equivalent of the herbicide per liter of composition.

DETAILED DESCRIPTION

The method comprises forming a mixture, i.e. a premix, of at least one alkali metal hydroxide and at least one further base selected from alkali metal hydroxides and nitrogen bases, and reacting the base premix with glyphosate acid.

The alkali metal hydroxides preferably include at least one selected from the group consisting of sodium hydroxide and potassium hydroxide.

The nitrogen bases may be selected from a range of compounds such as those of formula I:

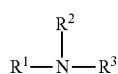

I wherein:
$R^1$ is selected from the group consisting of hydrogen, $C_1$ to $C_{10}$ alkyl, $C_1$ to $C_{10}$ alkanol and $C_1$ to $C_{10}$ amino alkyl;
$R^2$ and $R^3$ are independently selected from the group consisting of hydrogen, $C_1$ to $C_6$ alkyl, $C_1$ to $C_6$ alkanol, $C_1$ to $C_6$ amino alkyl and the group wherein $R^2$ and $R^3$ together complete a 5 or 6 numbered heterocyclic ring containing the nitrogen in formula I and optionally a further heteroatom selected from O and N as a ring member and optionally substituted by $C_1$ to $C_6$ alkyl. Examples of compounds of formula I in which R2 and R3 complete a heterocyclic ring include piperazine, morpholine and the N-alkyl derivatives thereof.

At least one nitrogen bases is preferably present and includes at least one selected from the group consisting of ammonia, $C_1$ to $C_{10}$ alkylamine, di-($C_1$ to $C_6$ alkyl)amine, tri-($C_1$ to $C_6$ alkyl)amine, $C_1$ to $C_{10}$ alkanolamine $C_1$ to $C_6$ alkyl($C_1$ to $C_6$ alkanol)amines and di-($C_1$ to $C_6$ alkyl)($C_1$ to $C_6$ alkanol)amines.

The nitrogen bases, in one set of embodiments contains at least one selected from the group consisting of ammonia, $C_1$ to $C_{10}$ alkylamine, di-($C_1$ to $C_4$ alkyl)amine, tri-($C_1$ to $C_4$ alkyl)amine, $C_1$ to $C_{10}$ alkanolamine $C_1$ to $C_4$ alkyl($C_1$ to $C_4$ alkanol)amines and di-($C_1$ to $C_4$ alkyl)($C_1$ to $C_4$ alkanol)amines.

Specific examples of readily available nitrogen bases include those selected from the group consisting of ammonia, methylamine, dimethylamine, trimethylamine, ethylamine, diethylamine, triethylamine, propylamine, dipropylamine, tripropylamine, isopropylamine, diisopropylamine, butylamine, dibutylamine, tributylamine, isobutylamine, diisobutylamine, triisobutylamine, 1-methylpropylamine (D,L), bis (1-methyl)propylamine (D,L), 1,1-dimethylethylamine, pentylamine, dipentylamine, tripentylamine, 2-pentylamine, 3-pentylamine, 2-methylbutylamine, 3-methylbutylamine, bis(3-methylbutyl)amine and tris(3-methylbutyl)amine.

Specific examples of the preferred nitrogen bases may be selected from the group consisting of ammonia, methylamine, isopropylamine, dimethylamine, diethylamine, diisopropylamine, triethylamine, triisopropylamine and dimethylethanolamine.

It is preferred that at least one nitrogen base is present in the premix and is a non-oxygen containing base such as those bases composed of nitrogen and at least one of nitrogen and hydrogen. Thus it is preferred at least one base of the premix is selected from the group consisting of ammonia, $C_1$ to $C_{10}$ alkylamine, di-($C_1$ to $C_4$ alkyl)amine and tri-($C_1$ to $C_4$ alkyl) amine. Specific examples of such bases include ammonia, methylamine, isopropylamine, dimethylamine, diethylamine, diisopropylamine, trimethylamine triethylamine, triisopropylamine)

In one set of embodiments the mixture of bases include at least one base other than ammonia and isopropylamine.

The mixture of the bases will preferably comprise at least 3% (preferably at least 5% and more preferably at least 10%) by weight of each of at least two bases. Further bases may be present in smaller amounts or in amounts in this range of 5% to 95% by weight if desired. In one embodiment there is an alkali metal hydroxide selected from potassium hydroxide and sodium hydroxide and a nitrogen base in a weight ratio in the range of from 10:90 to 90:10 such as from 20:80 to 80:20.

Some of the amines are volatile and in these circumstances it may be preferred to introduce the volatile amine to a less volatile amine or to form a mixture of amines in a suitable solvent. In this embodiment the efficiency of the method is generally significantly improved when compared with conventional processes as the loss of volatiles is significantly reduced thereby reducing costs and the problem of volatile emissions which are particularly problematic in industrial scale exothermic reactions such as the reaction of bases with glyphosate. Volatility is a potential issue in exothermic conditions for amines of boiling point up to 80° C. and in particular up to 60° C. such as up to 50° C. or up to 40° C. In the case of bases which are gaseous at room temperature such as ammonia and methylamine dissolution in a liquid nitrogen base optionally in the presence of a diluent such as water can improve significantly the efficiency with which the bases react with glyphosate acid.

The mixture of at least two bases including an alkali metal hydroxide and a further base selected from alkali metal hydroxides and nitrogen bases forms a premix composition, that is a mixture composition formed before mixing with the glyphosate acid. The premix is preferably a homogeneous mixture of the bases when it is added to the glyphosate acid.

Further bases and/or nitrogen containing adjuvants may be added to the compositions before or following the combination of the premix and glyphosate acid however the stoichiometry is preferably controlled to provide reaction of the base premix with at least the 50%, more preferably at least 80% and most preferably at least 90% of the glyphosate acid.

The glyphosate acid composition which is combined with the base premix may be in the form of a solid or may comprise a liquid. In one set of embodiments the glyphosate is a neat dry solid when combined with the base premix. In one embodiment the glyphosate acid is in the form of a solution in a suitable solvent for the glyphosate acid.

In one preferred set of embodiments the glyphosate acid composition combined with the nitrogen base premix comprises water. Glyphosate acid is conveniently manufactured in the form of a wetcake comprising glyphosate acid and residual water from the manufacturing process. The glyphosate acid used in the method may be the wetcake containing glyphosate. Typically the wetcake composition comprises, for example, at least 50% glyphosate such as at least 60%, at least 70% or at least 80% glyphosate. In one embodiment the glyphosate is in the form of a slurry containing glyphosate acid in particulate form and sufficient water to facilitate mixing and promote efficient reaction on combination with the base premix.

The method may involve addition of the base premix to glyphosate or addition of glyphosate to the premix. The two compositions, the base premix and glyphosate acid composition may also be simultaneously introduced to a reaction vessel. Generally addition of the base premix to glyphosate is preferred.

In a preferred set of embodiments the bases are added to the glyphosate acid aqueous composition in a mole ratio of total bases:glyphosate acid in the range of from 0.9 to 1.3, preferably 0.9 to 1.2, more preferably 0.9 to 1.13 and still more preferably 1.0 to 1.1.

The reaction between the glyphosate acid and the bases may be carried out at a range of temperatures such as from 5° C. to 90° C. and preferably from 5° C. to 60° C.

The mixture of bases may be added in a single addition, stepwise and may be added quickly or over a period of time. In some cases, particularly if the glyphosate is neat or in very concentrated suspension, there may be a significant exothermic reaction so that it may be appropriate to add the bases more slowly or to cool the reaction mixture. The composition of the mixture of bases may comprise a carrier such as water or other suitable liquid carrier to improve or vary the miscibility of the different bases. The presence of a carrier may also be used to dilute the bases and regulate the rate of addition and/or the homogeneity of mixing with the glyphosate acid.

The composition and method may utilize more than two bases such as three, four or five bases but typically the use of two or three bases is convenient. When used the further bases in addition to the two bases may be nitrogen bases and/or non-nitrogen bases such as alkali metal hydroxide or other metal bases.

On completion of the reaction the composition is a solution of the glyphosate in the form of a mixture of salts having a mixture of amine and alkali metal bases in the form of counter ions, which are generally cations, following neutralization of the glyphosate acid.

In general we have found that the viscosity of the aqueous glyphosate composition prepared by the process involving mixing the bases prior to reaction with glyphosate acid has a significantly lower viscosity than the corresponding composition formed by reacting each of the bases in sequence with glyphosate acid or from mixing the glyphosate salts formed with the corresponding counter ions provided by neutralization of glyphosate with the bases. The method also allows base combinations to be prepared which would not otherwise be available, for example because of high viscosity or poor stability, if bases were added sequentially rather than as a premix.

The composition is prepared by mixing the composition comprising the mixture bases with glyphosate acid. Generally the glyphosate acid will be present as a suspension or solid such as a precipitate in an aqueous composition. The concentration of the glyphosate acid will typically be at least 600 gae per liter of aqueous composition. The concentration of the glyphosate acid is preferably at least 610 gae/L preferably at least 620 gae/L, more preferably at least 630 gae/L and still more preferably at least 640 gae/L and most preferably at least 650 gae/L such as at least 650 gae/L, at least 700 gae/L, at least 750 gae/L and up to the limit of solubility. The optimum concentration of the acid composition will of course depend on the nature of the bases, their concentration and reaction conditions.

The method provides a significant advantage in the transport and handling of glyphosate concentrate. The ability to reduce significantly the viscosity of concentrates of a given loading or increase loading without the normal substantial increase in viscosity and consequential problems of instability and handling has significant economic benefits for the manufacturer and farmer. The cost of transport of a given active glyphosate quantity can be reduced and/or more economic pumping or dispensing equipment can be used. Accordingly, in one set of embodiments there is provided a method as hereinbefore described and further comprising loading the aqueous mixture of glyphosate salts into containers of volume in the range of 0.1 to 10,000 liters to substantially fill the containers, transporting the filled containers and dispensing the aqueous mixture of glyphosate salts from the containers. The aqueous mixture of glyphosate salts is preferably pumped into the containers.

The glyphosate concentrate may and preferably will comprise a surfactant. When used the surfactant component may be added at any time during the preparation process for example it may be present in the base mixture composition, in the glyphosate acid aqueous composition or may be added during and/or after reaction of the glyphosate acid with the mixture of amines.

The appropriate method will depend on the chemical nature of the surfactant and base reagents. For example, the caustic nature of alkali metal hydroxides generally means that addition with the base is undesirable particularly where such components react with or are decomposed by alkaline conditions.

The method may be used in preparing glyphosate compositions containing adjuvants and co-solvents, such as surfactants, antifoaming agents, glycols, stickers, penetrants drift reduction agents and water conditioners such as those selected from the group consisting of pH adjusters, buffering agents & AMADS (monocarbamide dihydrogen sulfate i.e. urea+sulfuric acid), isethonic acid and sulphated glycerine, and the like.

The method may also be used in preparation of concentrates to which such adjuvants may be added during tank mixing.

Thus, in one set of embodiments there is provided a kit for controlling plant growth comprising a first part comprising the concentrate composition prepared by the method hereinbefore described and a second part comprising an adjuvant composition for mixing with the concentrate on dilution with water such as in a spray tank prior to application to plants to be controlled.

The dilute compositions for application to plants whose growth is to be controlled may be prepared on site by the end-user shortly before application to the foliage of vegetation to be controlled, by mixing in the glyphosate concentrate prepared in accordance with the above method with an aqueous diluent. The aqueous diluent may further comprise a surfactant such as one or more of those described above. Such compositions are generally referred to as "tank-mix" compositions.

In the case of a solution concentrate adapted for simple dilution prior to application the composition will preferably comprise a surfactant. In this set of embodiments the concentration of the surfactant may be up to 30% by weight (preferably up to 25% by weight) of the aqueous composition. The range of surfactant concentrations may, for example be in the range of from 0.1 to 20% by weight of the aqueous composition and more preferably from 1 to 15% by weight of the aqueous composition.

The concentration of the surfactant may be up to 30% by weight of the aqueous composition preferably in the range of from 0.1 to 30% by weight of the aqueous composition and more preferably from 1 to 25% by weight of the aqueous composition. In one set of embodiments the total surfactant is present in an amount of no more than 20% by weight of the total aqueous glyphosate concentrate.

Amphiphilic agents which have been claimed to enhance the herbicidal efficacy of formulations comprising glyphosate salts include the following: quaternary ammonium surfactant; etheramine surfactants; alkylether and amine surfactant combinations; acetylenic diol and alkyl(poly)glycoside surfactant combinations; lipophilic fatty amine ethoxylate surfactants; alkoxylated amine surfactants; betaine surfactants; alkyl polyglycoside agents; secondary or tertiary alcohol surfactants; silicone copolymer wetting agents and trialkylamine oxide or quaternary amine or trialkylbetaine surfactant combinations; sorbitan fatty acid ester and amine, quaternary ammonium or alkylglycoside surfactant combinations; surfactants derived from alkanethiols; polyoxyalkylene trisiloxane surfactants; super-wetting agents such as silicone-based and fluorocarbon-based surfactants; supra-molecular aggregates comprising one or more amphiphilic salts having a glyphosate anion and cation derived by protonation of secondary or tertiary oily amines; alkoxylated primary alcohol surfactants; alkyl polysaccharide derivates; alkyl polyglycoside and ethoxylated alcohol combinations; alkylglucosides; surfactants comprising polyhydroxyhydrocarbyl and amine functionality; alkylglycoside and alkoxylated alkylamine surfactant combinations; alkyldiamine tetraalkoxylate surfactants; succinic acid derivatives; alkoxylated amido amines; sugar glycerides such as rapeseed oil sugar glyceride; diamine surfactants; widely-bridged alcohol polyethoxylates; water-soluble long-chain hydrocarbyl dimethylamine oxides and quaternary ammonium halide combinations; hydroxyalkylammonium adjuvants; polyether diamine surfactants; cationic, anionic, nonionic or zwitterionic silicone adjuvants; organosilicone surfactants and diphenyl oxide sulfonate surfactant combinations; a range of ether phosphate adjuvants; phosphourous surfactant adjuvants; polyglycerol and polyglycerol derivatives; $C_8$-$C_{22}$ sarcosinate or sarcosinate salts; ethoxylated vegetable oils; polyethoxylated dialkylamine surfactants; $C_{10}$-$C_{18}$ alkylpolyglycol ether sulfates; Sucrose & Sorbital Surfactants; Sorbitan Esters; Ethoxylated Saccahrose Esters; Coco Amido Propyl Dimethylamine Alkyldimethylamines; Phosphated Esters Tallow Amine Surfactants; Trisiloxanes; TEA and MDEA Esterquats; Dimethylethanolamine based Esterquats; Saccharides such as Alkyl Polysaccharide as well a glucosides; Alkyl Polypentosides (APP); Polyglycerines; Etheramine Alkoxylates; Sorbitan Monolaurate; Pine Terpinic compounds such oligomers etc (derived from alpha pinene & beta pinene)/Pine Oils; Cocoamine ethoxylates; Acrylates & Latex compounds; (Ethoxylated)Oleyl Alcohols; Alkylamine Alkoxylates; Etheramine Alkoxylates/Alkyl Etheramine; Quaternary Ammonium Salts/Ammonium Quaternary Derivatives; Quat Amines; Amine Oxides; Dialkoxylates Amines; Alkyl Alkoxylated Phosphates; Aminated Alkoxylated Alcohols; Dialkoxylated Amines; Carboxylates; Alkylethersulfates; Disodium sulfosuccinates/Succinates; Polyether Amines; Cocoamidopropyl betaines and salts of fatty acids.

Etheramine surfactants include surfactants having the representative chemical structure (a):

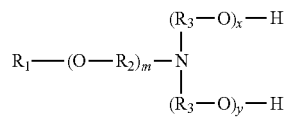

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene, and x and y are average numbers such that x+y is in the range from 2 to about 60; or (b):

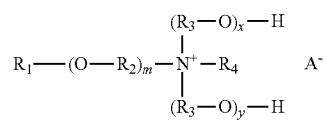

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene, $R_4$ is $C_1$-$C_4$ alkyl, x and y are average numbers such that x+y is in the range from 0 to about 60 and $A^-$ is an agriculturally acceptable anion; or (c)

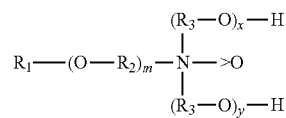

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene and x and y are average numbers such that x+y is in the range from 2 to about 60.

In one set of embodiments the glyphosate composition prepared by the method is substantially free of surfactants, prior to use, for example, when the concentrate is diluted with water in a spray tank prior to use.

In a further set of embodiments we provide a method for controlling plant growth comprising diluting the concentrate with water, optionally with addition of adjuvant, and applying the glyphosate to plants by, for example spray or application via a substrate on which the diluted composition is sorbed.

In a further set of embodiments the concentrate is applied without dilution by for example painting or contacting plants with a substrate such as a rope or wick on which the concentrate is absorbed.

One of the important advantages of the glyphosate compositions prepared according to the method is that the glyphosate concentration can be increased to very high levels, for example even over 600 gae/L, yet the surfactant concentration may still be included in a concentrate adequate to give excellent herbicidal performance without the end-user requiring to add more surfactant in the spray tank. In many cases the compositions prepared by the methods allow incorporation of surfactant which would not otherwise be possible for corresponding compositions prepared by combination of preformed salts or compositions prepared by sequential neutralization of glyphosate acid with different bases. In other cases the compositions prepared by the method provides handling characteristics such as pourability and pumping performance superior to the corresponding compositions prepared by combination of preformed salts or compositions prepared by sequential neutralization of glyphosate acid with different bases. The aqueous concentrates also generally have remarkably good storage stability under a wide range of temperature conditions despite the high loading of glyphosate and are generally superior to corresponding compositions prepared by combination of preformed salts of monobases (i.e. a glyphosate salt prepared using a single base in a separate vessel)

or compositions prepared by sequential neutralization of glyphosate acid with different bases.

Mixtures of glyphosate with other herbicides may also be prepared from the concentrated prepared by the method described above. Examples of such other herbicides include glufosinate, 2,4-D, MCPA, dicamba, diclorprop, diphenylethers, imidazolinones, sulfonylureas, other herbicides, insecticides, plant growth regulators and fungicides In one embodiment the method further comprises forming a mixture of at least one further acid herbicide with glyphosate acid and reacting the mixture of the at least two bases with the mixture of glyphosate acid and at least one other acid herbicide to provide a composition comprising a mixture of glyphosate salts and a mixture of salts of said at least one further herbicidal acid. The further acid herbicide will preferably comprise at least one acid group selected from phosphonic acid, sulfonic acid and carboxylic acid and preferably at least one carboxylic acid group.

The at least one further herbicidal acid may be selected from the group consisting of:
(i) benzoic acid herbicides such as acifluorfen chloramben; dicamba; 2,3,6-TBA; tricamba;
(ii) pyrimidinyloxybenzoic acid herbicides such as bispyribac and pyriminobac; pyrimidinylthio-benzoic acid herbicides such as pyrithiobac;
(iii) picolinic acid herbicides such as aminopyralid, clopyralid and picloram;
(iv) quinolinecarboxylic acid herbicides such as quinclorac and quinmerac;
(v) phenoxy acid herbicides such as 4-CPA, 2,4-D, 3,4-DA, MCPA and 2,4,5-T;
(vi) phenoxybutyric herbicides such as 4-CPB, 2,4-DB, 3,4-DB, MCPB and 2,4,5-TB;
(vii) phenoxypropionic herbicides such as cloprop, 4-CPP, dichlorprop, dechlorprop-P, fenoprop, mecoprop, mecoprop-P;
(viii) acid substituted diphenyl ether herbicide such as ethoxyfen;
(ix) aryloxy phonoxypropionic acid herbicides such as chlorazifop, clodinafop, clofop, flueroglycofen, cyhalofop, diclopfop, fenoxaprop, fenoxaprop-P, fenthiaprop, fluazifop, fheazifoop-P, haloxyfop, haloxyfop-P, isoxapyrifop, metamifop, propaquizafop, quizalofop, quizalofop-P and trifop;
(x) herbicides such as benzoylprop, aryalamine, flamprop and flamprop-M;
(xi) acid substituted nitro phenyl ether herbicides such as acifluorfen; and
(xii) organophosphorous herbicides other than glyphosate such as glufosinate and glufosinate-P The more preferred acid herbicides for use in the invention are selected from the group consisting of dicamba, aminopyralid, clopyralid, picloram, 2,4-D, MCPA, 2,4-DB, mecaprop, mecoprop-P, glufosinate, diclofop and fluazifop. Still more preferably, the one or more further acid herbicides when used with glyphosate acid are selected from the group consisting of dicamba, clopyralid, 2,4-D, MCPA and mecoprop.

Where there are a mixture of acid herbicides it is preferred that the glyphosate concentration in the final concentrate is at least 200 gae/L (preferably at least 360 gae/L, more preferably at least 450 gae/L) and the total acid herbicide salt in the final concentrate composition is at least 360 gae/L, more preferably at least 450 gae/L, still more preferably at least 550 gae/L and most preferably at least 600 gae/L.

When further acid herbicides are used in the process of the invention the glyphosate will typically comprise at least 20% by weight based on acid equivalent of the total acid herbicides preferably glyphosate acid will constitute at least 40% by weight, still more preferably at least 60% by weight and most preferably at least 80% by weight of the total acid herbicides including glyphosate.

In one embodiment, the glyphosate acid constitutes at least 95% more preferably at least 98% of the total acid herbicides (including glyphosate).

In a further embodiment, the glyphosate composition mixed with the mixture of at least two bases is free of other herbicidal acids.

In the embodiments in which a mixture of acid herbicides including glyphosate are reacted with the mixture of at least two bases it is preferred that the molar ratio of total alkali metal hydroxides and nitrogen bases:total acid herbicides is in the range of 0.9:1 to 1.3:1.

Methods of use of glyphosate formulations are well known to those of skill in the art. Aqueous concentrate compositions prepared by the method may be diluted in an appropriate volume of water and applied, for example by spraying, to unwanted vegetation to be controlled. Compositions prepared by the method may be applied at glyphosate ae rates in the range of for example from about 0.1 to about 5 kgae/ha, occasionally more. Typical glyphosate ae rates for control of annual and perennial grasses and broadleaves are in the range from about 0.25 to about 3 kgae/ha. Compositions of the invention may be applied in any convenient volume of water, most typically in the range from about 30 to about 2000 l/ha. Compositions prepared by the method of the invention also include solutions which may be applied by spraying for example. In these solutions, the concentration of glyphosate is selected according to the volume per unit area of spray solution to be used and the desired rate of application of glyphosate per unit area. For example, conventional spraying is done at 30 to 2000 liters (particularly 50-600 liters) of spray solution per hectare, and the rate of application of glyphosate is typically 0.125 to 1.5 kg of glyphosate acid equivalent per hectare. Spray solution compositions can be prepared by diluting the aqueous liquid concentrates preferably comprising surfactant adjuvants or by tank mixing the aqueous concentrates formed by the method with adjuvants as described above.

The invention will now be described with reference to the following examples. It is to be understood that the examples are provided by way of illustration of the invention and that they are in no way limiting to the scope of the invention.

EXAMPLES

Compositions of glyphosate salts were prepared from glyphosate acid using the bases identified in Table 1 added in accordance with (A) comparative process in which bases were reacted with glyphosate acid by "separate" addition of the bases in sequence and (B) a process in accordance with the invention in which the bases were "mixed" and the mixture of bases added to an aqueous slurry of glyphosate acid.

(A) In the "separate" addition process the bases identified in the table were separately added in sequence in the molar base ratio identified the Table 1 to an aqueous slurry of glyphosate acid in an amount to neutralise the glyphosate acid. Where indicated in the table a surfactant was used and was added to the composition following neutralisation of the glyphosate acid. The final composition had a glyphosate concentration based on glyphosate acid equivalent indicated in the table expressed in grams of glyphosate acid equivalent per liter of composition (gae/L Glyphosate Acid).

(B) In the mixed addition process the bases shown in Table 1 were mixed in the molar ratios indicated and were added to an aqueous slurry of glyphosate acid in an amount to neutralise the glyphosate acid (equimolar amount). Where indicated in the table a surfactant was used and was added to the composition following neutralisation of the glyphosate acid.

The final composition had a glyphosate concentration based on glyphosate acid equivalent indicated in the table expressed in grams of glyphosate acid equivalent per liter of composition (gae/l Glyphosate).

In Table 1 the following abbreviations are used for the bases which are used to form glyphosate counter ions:
MMA—monomethylamine
MIPA—monoisopropylamine
NH3—ammonia
TEA—triethylamine
KOH—potassium hydroxide
NaOH—sodium hydroxide
MEA—monoethanolamine
DMA—dimethylamine Testing Each of the compositions prepared by (A) the separate addition of bases and (B) the mixed addition of bases were subject to testing to determine the assay results reported in the table in the following procedures:

In the Examples pH was determined by the method described in CIPAC MT_75.3 at 5% w/V in deionised water. Viscosity was determined at 5° C. and at 20° C.

The viscosity of compositions was measured after equilibrating the composition at the respective temperatures using a Brookfield viscometer (model DV-1) Spindle 21 in a fixed volume temperature controlled cylinder to ensure direct comparability.

TABLE 1

| Ex | base | base ratio | process | gae/L Glyphosate | Surfactant | Surfactant g/L | 5% pH | Viscosity mPa·s 5° C. | Viscosity mPa·s 20° C. |
|---|---|---|---|---|---|---|---|---|---|
| Ex1 | MMA/MIPA/KOH | 45/10/45 | premix | 650 | None | 0 | 4.5 | 312 | 143 |
| CE1 | MMA/MIPA/KOH | 45/10/45 | separate | 650 | None | 0 | 4.49 | 328.4 | 147 |
| Ex2 | MMA/MIPA/KOH | 50/20/30 | premix | 650 | None | 0 | 4.4 | 332.8 | 139.7 |
| CE2 | MMA/MIPA/KOH | 50/20/30 | separate | 650 | None | 0 | 4.51 | 401.1 | 155.7 |
| Ex3 | MMA/MIPA/KOH | 50/20/30 | premix | 570 | Surf A | 140 | 4.45 | 671.4 | 268 |
| CE3 | MMA/MIPA/KOH | 50/20/30 | separate | 570 | Surf A | 140 | 4.55 | 837.9 | 282 |
| Ex4 | MEA/KOH | 45/55 | premix | 650 | None | 0 | 4.54 | 411.2 | 154.9 |
| CE4 | MEA/KOH | 45/55 | separate | 650 | None | 0 | 4.43 | 528.7 | 188.9 |
| Ex5 | MEA/KOH | 45/55 | premix | 570 | Surf A | 140 | 4.59 | 361.3 | 198 |
| CE5 | MEA/KOH | 45/55 | separate | 570 | Surf A | 140 | 4.49 | 401.1 | 212 |
| Ex6 | MMA/KOH | 55/45 | premix | 723 | None | 0 | 4.45 | 510.2 | 187 |
| CE6 | MMA/KOH | 55/45 | separate | 723 | None | 0 | 4.45 | 538.3 | 199 |
| Ex7 | MMA/KOH | 55/45 | premix | 650 | None | 0 | 4.47 | 213.1 | 97.2 |
| CE7 | MMA/KOH | 55/45 | separate | 650 | None | 0 | 4.42 | 229 | 108 |
| Ex8 | MMA/KOH | 55/45 | premix | 650 | Surf B | 100 | 4.51 | 503.4 | 76 |
| CE8 | MMA/KOH | 55/45 | separate | 650 | Surf B | 100 | 4.41 | 568.1 | 197 |
| Ex9 | NaOH/KOH | 15/85 | premix | 650 | None | 0 | 4.46 | 138.2 | 60.1 |
| CE9 | NaOH/KOH | 15/85 | separate | 650 | None | 0 | 4.40 | 140.5 | 61.8 |
| Ex10 | NaOH/KOH | 15/85 | premix | 650 | Surf B | 200 | 4.54 | 814 | 249 |
| CE10 | NaOH/KOH | 15/85 | separate | 650 | Surf B | 200 | 4.45 | 861 | 256 |

Surf. A Quaternary amine surfactant
Surf. B Tallow amine surfactant blend

Example 11 and Comparative Example 11

Monobasic Glyphosate Combinations Compared with Base Premix

The mixed salt batch of Example 11 was prepared by reacting a premix of MEA and KOH in the ratio shown in Table 2 with glyphosate acid to provide mixed glyphosate salts in the final concentrate with a concentration of 600 gae/L.

The mixed salt batch CE11 was made by adding (a) the monoethanolamine salt of glyphosate and (b) the potassium salt of glyphosate monobase batches together in the ratios shown below in Table 2 and mixed for 20 minutes before testing. The monobases were prepared by:
(a) using MEA to neutralize glyphosate acid at 600 g/L (84.6% glyphosate wet cake), and
(b) using KOH to neutralize glyphosate 600 g/L (84.6% glyphosate wet cake)

TABLE 2

| Ex | glyphosate gae/L | Base ratio | Bases | Process | Viscosity mPa·s 5° C. | Viscosity mPa·s 20° C. |
|---|---|---|---|---|---|---|
| CE11(a)/(b) | 600 | 55/45 | MEA/KOH | monobase | 226 | 89.8 |
| Ex11 | 600 | 55/45 | MEA/KOH | premix | 76.4 | 36.3 |

Table 2 shows that the viscosity of the composition resulting from reacting a base premix is significantly less notwithstanding that the composition of the final concentrate equivalent.

Example 12 and Comparative Example 12

This example demonstrates preparation of a mixture of salts from glyphosate acid in the presence of a further acid herbicide, dicamba.

Example 12 was prepared in accordance with the invention by forming a premix of bases shown in Table 3 in the molar ratios listed and reacting the premix with a mixture of glyphosate acid and dicamba acid to provide the concentration gae/L of mixed salts of glyphosate and mixed salts of dicamba shown.

The process of CE 12 was to individually prepare (a) potassium salt of a mixture of glyphosate and dicamba and (b) monoethanolamine salt of a mixture of glyphosate and dicamba and combine the two salt compositions to provide a mixture of potassium and monoethanolamine salts of both glyphosate and dicamba in the concentration in the final concentrate composition as shown in gae/L.

TABLE 3

| Example No. | gae/L Glyphosate | gae/L Dicamba | Base Mixing | Bases | Base Ratio | Viscosity 5° C. cp | Viscosity 20° C. cp | Appearance | SG | pH |
|---|---|---|---|---|---|---|---|---|---|---|
| Ex 12 | 220 | 220 | Premix | KOH/MEA | 50/50 | 32 | 17.2 | Clear sol | 1.286 | 8.85 |
| CE12 | 220 | 220 | Separate | KOH/MEA | 50/50 | 45.1 | 22 | Clear sol | 1.285 | 9 |

The concentrate prepared in accordance with the method of the invention (Ex12) has a significantly lower viscosity than the comparison (CE12) not withstanding that the compositions are otherwise equivalent.

The invention claimed is:

1. A method for preparing an aqueous mixture of glyphosate salts to improve the handling of the mixture, the method comprising:
   forming a homogeneous mixture of at least two bases comprising at least one alkali metal hydroxide, and at least one further base selected from the group consisting of alkali metal hydroxides and nitrogen bases and
   reacting the homogeneous mixture with glyphosate acid in an aqueous reaction medium to provide an aqueous mixture of glyphosate salts wherein the concentration of glyphosate (based on glyphosate acid equivalent) is at least 500 gae/L, and wherein the nitrogen base includes at least one nitrogen base selected from the group consisting of ammonia, $C_1$ to $C_{10}$ alkylamine, di-($C_1$ to $C_6$ alkyl)amine and tri-($C_1$ to $C_6$ alkyl)amine and wherein when the homogeneous mixture includes potassium hydroxide and either ammonia or isopropylamine then at least one further base is present selected from the group consisting of said alkali metal hydroxide, ammonia, $C_1$ to $C_{10}$ alkylamine, di-($C_1$ to $C_6$ alkyl)amine and tri-($C_1$ to $C_6$ alkyl)amine, and wherein the aqueous mixture has a mole ratio of total of alkali metal hydroxide and nitrogen bases to glyphosate acid that is in the range of from 0.9:1 to 1.3:1.

2. The method according to claim 1 wherein the at least one alkali metal hydroxide is selected from the group consisting of sodium hydroxide, potassium hydroxide and lithium hydroxide.

3. The method according to claim 1 wherein the homogeneous mixtures of at least two bases comprises at least two alkali metal hydroxides selected from the group consisting of sodium hydroxide, potassium hydroxide and lithium hydroxide.

4. The method according to claim 1 wherein the concentrate of glyphosate salts is at least 550 gae/L.

5. The method according to claim 1 wherein the concentration of the glyphosate is at least 600 gae/L.

6. The method according to claim 1 wherein the concentration of glyphosate is at least 610 gae/L.

7. The method according to claim 1 wherein the concentration of glyphosate is at least 620 gae/L.

8. The method according to claim 1 wherein the nitrogen bases comprise at least one of methylamine, dimethylamine, isopropylamine, diisopropylamine and triethylamine.

9. The method according to claim 1 wherein the homogeneous mixture of at least two bases includes at least one selected from the group consisting of sodium hydroxide, methylamine, dimethylamine and triethylamine.

10. The method according to claim 1 comprising loading the aqueous mixture of glyphosate salts into containers of volume in the range of 0.1 to 10,000 liters to substantially fill the containers, transporting the filled containers and dispensing the aqueous mixture of glyphosate salts from the containers.

11. The method according to claim 10 wherein the aqueous mixture of glyphosate salts is pumped into the containers.

12. The method according to claim 1 wherein the reaction between the glyphosate acid and bases is carried out at a temperature in the range of from 5° C. to 80° C.

13. The method according to claim 1 wherein the method further comprises forming a mixture of at least one further acid herbicide with glyphosate acid and reacting the homogeneous mixture of the at least two bases with the mixture of glyphosate acid and at least one other acid herbicide to provide a composition comprising a mixture of glyphosate salts and a mixture of the at least one further acid herbicide salt, wherein the composition has a concentration of glyphosate salts that is at least 500 gae/L and a molar ratio of total of alkali metal hydroxide and nitrogen bases to total acid herbicides in the range of from 0.9:1 to 1.3:1.

14. The method according to claim 13 wherein the at least one acid herbicide is selected from the group consisting of dicamba, clopyralid, 2,4-D, MCPA and mecoprop.

15. The method according to claim 13 wherein the glyphosate acid comprises at least 80% by weight of the total acid herbicide including glyphosate acid.

16. The method according to claim 1 further comprising addition of a surfactant wherein the concentration of the surfactant is in the range of from 0.1 to 20% by weight of the aqueous glyphosate concentrate composition.

17. The method according to claim 16 wherein the surfactant comprises one or more selected from the group consisting of quaternary ammonium surfactant; etheramine surfactants; alkylether and amine surfactant combinations; acetylenic diol and alkyl(poly)glycoside surfactant combinations; lipophilic fatty amine ethoxylate surfactants; alkoxylated amine surfactants; betaine surfactants; alkyl polyglycoside agents; secondary or tertiary alcohol surfactants; silicone copolymer wetting agents and trialkylamine oxide or quaternary amine or trialkylbetaine surfactant combinations; sorbitan fatty acid ester and amine, quaternary ammonium or alkylglycoside surfactant combinations; surfactants derived from alkanethiols; polyoxyalkylene trisiloxane surfactants; super-wetting agents comprising silicone-based and fluorocarbon-based surfactants; supra-molecular aggregates comprising one or more amphiphilic salts having a glyphosate anion and cation derived by protonation of secondary or tertiary oily amines; alkoxylated primary alcohol surfactants; alkyl polysaccharide derivates; alkyl polyglycoside and ethoxylated alcohol combinations; alkylglucosides; surfactants comprising polyhydroxyhydrocarbyl and amine functionality; alkylglycoside and alkoxylated alkylamine surfactant combinations; alkyldiamine tetraalkoxylate surfactants; succinic acid derivatives; alkoxylated amido amines; sugar glycerides; diamine surfactants; widely-bridged alcohol polyethoxylates; water-soluble long-chain hydrocarbyl dimethylamine oxides and quaternary ammonium halide combinations; hydroxyalkylammonium adjuvants; polyether diamine surfactants; cationic, anionic, nonionic or zwitterionic silicone adjuvants; organosilicone surfactants and diphenyl oxide sulfonate surfactant combinations; a range of ether phosphate adjuvants; phosphorous surfactant adjuvants; polyglycerol and polyglycerol derivatives; C8-C22 sarcosinate or sarcosinate salts; ethoxylated vegetable oils; polyethoxylated dialkylamine surfactants; C10-C18 alkylpolyglycol ether sulfates; Sucrose & Sorbital Surfactants; Sorbitan Esters; Ethoxylated Saccahrose Esters; Coco Amido Propyl Dimethylamine Akyldimethylamines; Phosphated Esters Tallow Amine Surfactants; Trisiloxanes; TEA and MDEA Esterquats; Dimethylethanolamine based Esterquats; Saccharides; Alkyl Polypentosides (APP); Polyglycerines; Etheramine Alkoxylates; Sorbitan Monolaurate; Pine Terpinic compounds; Cocoamine ethoxylates; Acrylates & Latex compounds; (Ethoxylated)Oleyl Alcohols; Alkylamine Alkoxylates; Etheramine Alkoxylates/Alkyl Etheramine; Quaternary Ammonium Salts/Ammonium Quaternary Derivatives; Quat Amines; Amine Oxides; Dialkoxylates Amines; Alkyl Alkoxylated Phosphates; Aminated Alkoxylated Alcohols; Dialkoxylated Amines; Carboxylates; Alkylethersulfates; Disodium sulfosuccinates/Succinates; Polyether Amines; Cocoamidopropyl betaines and salts of fatty acids.

18. The method according to claim 1, wherein said forming the homogeneous mixture and said reacting the homogeneous mixture with glyphosate acid improves the handling of the resulting aqueous concentrate by reducing the viscosity of the aqueous concentrate as compared to an aqueous concentrate containing the same concentration of glyphosate salt which is formed by either (i) sequential mixing of the at least two bases with glyphosate acid or (ii) mixing preformed glyphosate salts of the at least two bases.

* * * * *